(12) United States Patent
Mazzei et al.

(10) Patent No.: US 6,840,903 B2
(45) Date of Patent: Jan. 11, 2005

(54) LARYNGOSCOPE WITH IMAGE SENSOR

(75) Inventors: William J. Mazzei, San Diego, CA (US); Terence M. Davidson, Poway, CA (US); Steven P. Richieri, San Diego, CA (US)

(73) Assignee: Nuvista Technology Corporation, La Jolla, CA (US)

( * ) Notice: Subject to any disclaimer, the term of this patent is extended or adjusted under 35 U.S.C. 154(b) by 0 days.

(21) Appl. No.: 10/102,800

(22) Filed: Mar. 21, 2002

(65) Prior Publication Data

US 2003/0181789 A1 Sep. 25, 2003

(51) Int. Cl.[7] ............................................... A61B 1/267
(52) U.S. Cl. ........................ 600/188; 600/185; 600/190
(58) Field of Search ........................ 600/185, 187–190, 600/193, 194, 197–200

(56) References Cited

U.S. PATENT DOCUMENTS

| | | |
|---|---|---|
| 2,769,441 A | 11/1956 | Abramson |
| 2,800,344 A | 7/1957 | Wolcott |
| 3,766,909 A | 10/1973 | Ozbey |
| 3,884,222 A | 5/1975 | Moore |
| 3,900,021 A | 8/1975 | Makepeace et al. |
| 3,943,920 A | 3/1976 | Kandel |
| 4,086,919 A | 5/1978 | Bullard |
| 4,126,127 A | 11/1978 | May |
| 4,273,112 A | 6/1981 | Heine et al. |
| 4,294,235 A | 10/1981 | Storz |
| 4,295,465 A | * 10/1981 | Racz et al. .................. 600/192 |
| 4,305,386 A | 12/1981 | Tawara |
| 4,306,547 A | 12/1981 | Lowell |
| 4,323,304 A | 4/1982 | Ishii |
| 4,337,761 A | 7/1982 | Upsher |
| 4,360,008 A | 11/1982 | Corazzelli, Jr. |
| 4,406,280 A | 9/1983 | Upsher |
| 4,413,278 A | 11/1983 | Feinbloom |
| 4,437,458 A | 3/1984 | Upsher |
| 4,484,896 A | 11/1984 | Kohnke |

(List continued on next page.)

FOREIGN PATENT DOCUMENTS

| | | |
|---|---|---|
| DE | 32 17 476 A1 | 5/1982 |
| DE | 41 32 687 A1 | 10/1991 |
| DE | 199 55 180 A1 | 11/1999 |
| EP | 0 030 014 B1 | 3/1986 |
| EP | 0 110 333 B1 | 6/1987 |
| EP | 0 282 832 A1 | 9/1988 |
| EP | 0 184 588 B1 | 3/1989 |
| EP | 0 465 942 A1 | 1/1992 |
| EP | 0 653 180 B1 | 5/1995 |
| EP | 0 901 772 B1 | 7/1998 |
| EP | 1 062 905 A1 | 12/2000 |
| EP | 1 064 878 A2 | 1/2001 |
| GB | 2 191 949 A | 12/1987 |
| GB | 2 209 944 A | 6/1989 |
| WO | WO 89/02719 | 4/1989 |
| WO | WO 91/12044 | 8/1991 |
| WO | WO 93/11700 | 6/1993 |
| WO | WO 93/20893 | 10/1993 |
| WO | WO 94/09695 | 5/1994 |
| WO | WO 94/09701 | 5/1994 |
| WO | WO 98/26706 | 6/1994 |
| WO | WO 94/14368 | 7/1994 |

(List continued on next page.)

*Primary Examiner*—Michael Peffley
(74) *Attorney, Agent, or Firm*—Cooley Godward LLP

(57) ABSTRACT

A laryngoscope and viewing system configured to provide imaging of a patient's airway passage during intubation is described. In one embodiment, the described device includes a handle; a blade attached to the handle, a flange attached to one side of the blade; a transmission cable connected to the opposite side of the blade; and a camera connected to the transmission cable, wherein the camera is offset from the blade in at least one of the X plane and the Y plane.

31 Claims, 5 Drawing Sheets

U.S. PATENT DOCUMENTS

| | | | |
|---|---|---|---|
| 4,491,865 | A | 1/1985 | Danna et al. |
| 4,527,553 | A | 7/1985 | Upsher |
| 4,546,762 | A | 10/1985 | Upsher |
| 4,557,256 | A | 12/1985 | Bauman |
| 4,565,187 | A | 1/1986 | Soloway |
| 4,573,451 | A | 3/1986 | Bauman |
| 4,575,784 | A | 3/1986 | Diau |
| 4,592,343 | A | 6/1986 | Upsher |
| 4,651,202 | A | 3/1987 | Arakawa |
| 4,736,734 | A | 4/1988 | Matsuura et al. |
| 4,807,594 | A | 2/1989 | Chatenever |
| 4,815,451 | A | 3/1989 | Bauman |
| 4,844,071 | A | 7/1989 | Chen et al. |
| 4,877,016 | A | 10/1989 | Kantor et al. |
| 4,878,485 | A | 11/1989 | Adair |
| 4,901,708 | A | 2/1990 | Lee |
| 4,905,669 | A | 3/1990 | Bullard et al. |
| 4,918,521 | A | 4/1990 | Yabe et al. |
| 4,924,855 | A | 5/1990 | Salerno et al. |
| 4,947,896 | A | 8/1990 | Bartlett |
| 4,958,624 | A | 9/1990 | Stone et al. |
| 4,982,729 | A | 1/1991 | Wu |
| 4,989,586 | A | 2/1991 | Furukawa |
| 5,003,963 | A | 4/1991 | Bullard et al. |
| 5,101,807 | A | 4/1992 | Kawashima |
| 5,178,132 | A | 1/1993 | Mahefky |
| 5,183,031 | A | 2/1993 | Rossoff |
| 5,203,320 | A | 4/1993 | Augustine |
| 5,263,472 | A | 11/1993 | Ough |
| 5,279,281 | A | 1/1994 | Harvey |
| 5,349,943 | A | 9/1994 | Ruiz |
| 5,355,870 | A | 10/1994 | Lacy |
| 5,363,838 | A | 11/1994 | George |
| 5,363,839 | A | 11/1994 | Lankford |
| 5,363,840 | A | 11/1994 | Silva |
| 5,381,787 | A | 1/1995 | Bullard |
| 5,408,992 | A | 4/1995 | Hamlin et al. |
| 5,425,356 | A | 6/1995 | Ough |
| 5,443,058 | A | 8/1995 | Ough |
| 5,494,483 | A | 2/1996 | Adair |
| 5,498,231 | A | 3/1996 | Franicevic |
| 5,527,261 | A | 6/1996 | Monroe et al. |
| 5,529,570 | A | 6/1996 | Storz |
| 5,591,119 | A | 1/1997 | Adair |
| 5,603,688 | A | 2/1997 | Upsher |
| 5,630,783 | A | 5/1997 | Steinberg |
| 5,643,221 | A | 7/1997 | Bullard |
| 5,651,761 | A | 7/1997 | Upsher |
| 5,701,904 | A | 12/1997 | Simmons et al. |
| 5,702,351 | A | 12/1997 | Bar-Or et al. |
| 5,776,052 | A | 7/1998 | Callahan |
| 5,800,344 | A * | 9/1998 | Wood et al. ............... 600/188 |
| 5,819,727 | A | 10/1998 | Linder |
| 5,827,178 | A * | 10/1998 | Berall ............... 600/185 |
| 5,845,634 | A | 12/1998 | Parker |
| 5,846,183 | A | 12/1998 | Chilcoat |
| 5,846,186 | A | 12/1998 | Upsher |
| 5,873,818 | A * | 2/1999 | Rothfels ............... 600/188 |
| 5,879,304 | A | 3/1999 | Shuchman et al. |
| 5,888,193 | A | 3/1999 | Breidenthal et al. |
| 5,897,489 | A | 4/1999 | Urbanowicz et al. |
| 5,897,491 | A | 4/1999 | Kastenbauer et al. |
| 5,906,576 | A | 5/1999 | Upsher |
| 5,913,816 | A | 6/1999 | Sanders et al. |
| 5,921,917 | A | 7/1999 | Barthel et al. |
| 5,941,816 | A | 8/1999 | Barthel et al. |
| 5,951,461 | A | 9/1999 | Nyo et al. |
| 5,954,632 | A | 9/1999 | Heckele et al. |
| 5,973,728 | A | 10/1999 | Levitan |
| 5,993,383 | A | 11/1999 | Haase |
| 6,004,263 | A | 12/1999 | Nakaichi et al. |
| 6,013,026 | A | 1/2000 | Krauter et al. |
| 6,036,639 | A | 3/2000 | Allred, III et al. |
| 6,083,151 | A | 7/2000 | Renner et al. |
| 6,090,040 | A | 7/2000 | Metro |
| 6,095,972 | A | 8/2000 | Sakamoto |
| 6,123,666 | A * | 9/2000 | Wrenn et al. ............... 600/188 |
| 6,135,948 | A | 10/2000 | Lee |
| 6,139,491 | A | 10/2000 | Heine et al. |
| 6,146,402 | A | 11/2000 | Munoz |
| 6,186,944 | B1 * | 2/2001 | Tsai ............... 600/200 |
| 6,217,514 | B1 | 4/2001 | Gruen et al. |
| 6,248,061 | B1 | 6/2001 | Cook, Jr. |
| 6,251,069 | B1 | 6/2001 | Mentzelopoulos et al. |
| 6,277,068 | B1 | 8/2001 | Wojnowicz et al. |
| 6,350,235 | B1 * | 2/2002 | Cohen et al. ............... 600/199 |
| 6,354,993 | B1 * | 3/2002 | Kaplan et al. ............... 600/188 |
| 2001/0014768 | A1 | 8/2001 | Kaplan et al. |

FOREIGN PATENT DOCUMENTS

| | | |
|---|---|---|
| WO | WO 98/46121 | 10/1998 |
| WO | WO 99/29228 | 6/1999 |
| WO | WO 99/44490 | 9/1999 |
| WO | WO 01/78582 A1 | 10/2001 |
| WO | WO 01/78583 A2 | 10/2001 |

* cited by examiner

LARYNGOSCOPE WITH IMAGE SENSOR

FIELD OF THE INVENTION

The present invention relates generally to medical devices. In particular, but without limitation, the present invention relates to a laryngoscope and viewing system configured to provide imaging of a patient's airway passage during intubation and similar medical procedures.

BACKGROUND OF THE INVENTION

In a process known as "intubation," an endotracheal tube is inserted into a patient's airway passage to facilitate breathing during certain medical procedures. To avoid damaging the airway passage while inserting the endotracheal tube, medical professionals generally use a laryngoscope to open and view the airway passage and to secure the patient's tongue to one side of the mouth. A typical laryngoscope includes a rigid, curved structure with a smooth tip that engages the tissue of the patient's tongue and airway passage. Laryngoscopes often also include a guide surface for directing the endotracheal tube as it is inserted into the airway passage.

Even with the use of a laryngoscope, medical professionals often damage a patient's airway passage when inserting the endotracheal tube. The reasons that medical professionals damage the airway passage center is their inability to monitor the laryngoscope and endotracheal tube as it is being inserted. To reduce the risk to patients, several modified laryngoscopes have been made. These laryngoscopes, however, are not completely satisfactory. Certain devices, for example, require two people for proper operation—a first person to insert a fiber optic or camera device into the patient's airway and a second person to operate the laryngoscope and insert the endotracheal tube.

Other systems include an integrated laryngoscope and imaging device. These systems generally come in two forms: those with integrated viewing devices and those without integrated viewing devices. Laryngoscopes with the integrated viewing device generally include a small screen attached directly to the handle of the laryngoscope. A medical professional can insert the laryngoscope into the patient's airway passage so that the imaging device captures a corresponding image thereof. The medical professional can then view the airway passage and guide the endotracheal tube to its proper location therein. By having the viewing screen attached directly to the laryngoscope, the medical professional is not forced to shift his field of vision away from the patient to monitor the insertion of the tube.

The laryngoscope with the non-integrated viewing device operates in much the same way as the laryngoscope with the integrated viewing device. The primary difference being that the laryngoscope with the non-integrated viewing device transmits the image of the airway passage to a remote viewing device such as a video monitor. The medical professional can then view the insertion of the endotracheal tube on the remote viewing device.

Although the laryngoscope with the integrated camera system contains some improvements over the basic laryngoscope, these systems are not always satisfactory. For example, in present systems, the view from the laryngoscope's camera becomes blocked as the endotracheal tube passes the end of the laryngoscope. Unfortunately, when the camera's view is blocked, the health care professional is "blind" and prone to damaging the patient's airway passage. Accordingly, a system and method are needed to address the above-described problems as well as other problems with existing laryngoscope technology.

SUMMARY OF THE INVENTION

Exemplary embodiments of the present invention that are shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents and alternative constructions that fall within the spirit and scope of the invention as expressed in the claims.

In one embodiment, the present invention includes a laryngoscope integrated with an imaging device such as a camera. The laryngoscope of this embodiment includes a blade for insertion into the patient's airway passage. This blade can be permanently affixed to a handle or can be removably mounted so that different blades can be connected to the handle. On one side of the blade—generally the left side—is a flange that sits perpendicular to the blade. The blade secures the patient's tongue to one side of the mouth and provides a surface for the endotracheal tube to engage as it is inserted into the airway. For proper perspective, the laryngoscope should be viewed with the handle up, the blade down and away.

The blade also includes an imaging device that can be connected externally to the blade or integrated into the blade and/or flange. Generally, the imaging device is positioned adjacent to the blade and the left side of the flange. Moreover, the end portion of the imaging device can be partially disengaged from the blade (or flange) to provide a better angle for viewing the patient's airway passage. For example, the image collection point for the imaging device could be offset from the blade in both the X plane and the Y plane. Depending upon the embodiment, the imaging device could be rigid so that the offset is fixed, or the imaging device could be flexible so that the offset is variable.

In other embodiments, the laryngoscope is equipped with a wireless transmitter for relaying images of the airway passage to a remote viewing device. Alternatively, the imaging device could be attached to the remote viewing device by a traditional wired connection. In yet another embodiment, the viewing device could be directly attached to the handle of the laryngoscope.

DETAILED DESCRIPTION

Figure 1:
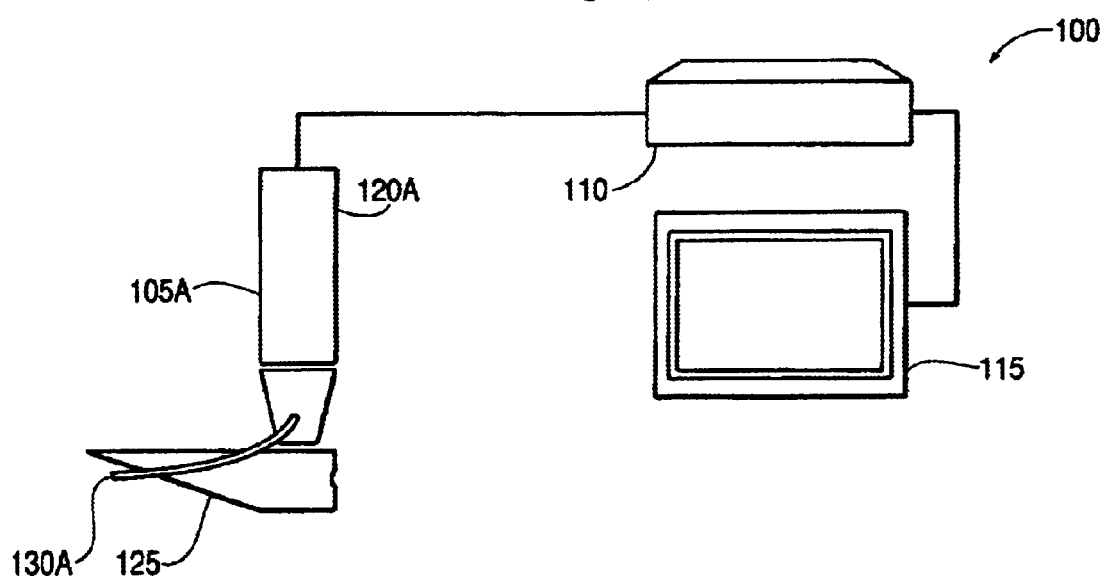
FIG. 1 illustrates a system constructed in accordance with the present invention.

Referring to FIG. 1, it illustrates a system 100 constructed in accordance with one embodiment of the present invention. In this embodiment, an optically-enabled laryngoscope 105A is connected to a camera controller 110 and a remote viewing device 115 such as a TV or video monitor. In operation, the medical professional grasps the handle 120A of the laryngoscope 105A and inserts the blade portion 125 into the patient's airway passage. The camera 130A that is fixed to the blade 125 can then capture an image of the airway passage and transmit that image to the camera controller 110 for display at the remote viewing device 115. The medical professional can then use the displayed image to guide an endotracheal tube into the patient's airway passage.

Figure 2:
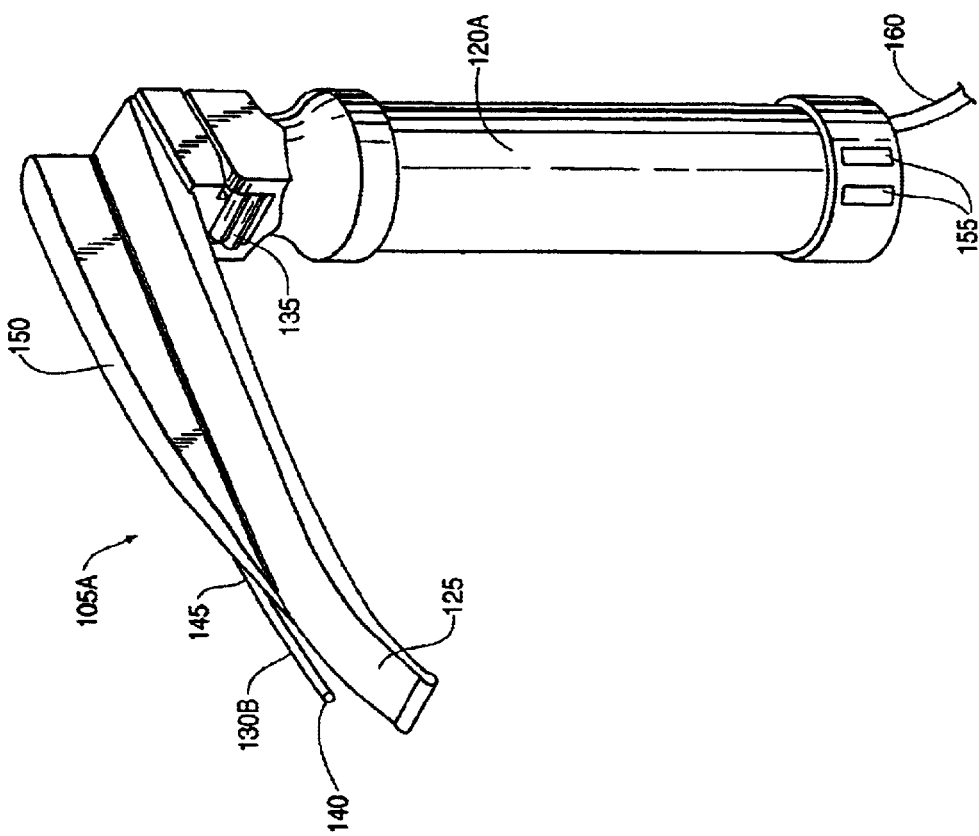
FIG. 2 illustrates one embodiment of a laryngoscope in accordance with the present invention.

Referring now to FIG. 2, it illustrates one embodiment of a laryngoscope 105A in accordance with the principles of the present invention. In this embodiment, a removable blade 125 is attached to a handle 120A by the coupler 135, which provides a reliable connection for connecting the blade-mounted camera unit 130B with corresponding circuitry (not shown) in the handle 120A. Although the exemplary embodiments are described with relation to a camera, embodiments of the present invention can include fiber optic bundles (which transmit images back to a camera mounted near the handle-end of the blade or in the handle), endoscope, or any other imaging device. The camera unit 130B, in one embodiment, can include a camera 140, a connection mechanism 145, and a light (not shown). The camera portion 140 of the camera unit generally can be any one of the small camera units that are widely available. Moreover, the camera unit 130B could be either a fixed-focus or a variable-focus unit, a straight lens unit, or an angulated lens unit. Although the camera unit 130B is shown as secured to the outer edge of the blade 125, portions of the camera unit 130B can be housed inside the blade 125 or the flange 150 or secured to the flange 150.

In addition to the camera unit 130B, the blade 125 also includes a flange 150 that is typically arranged perpendicular to the surface of the blade 125. The flange 150 is used to secure the patient's tongue away from the endotracheal tube. In particular, the flange 150 can be on the left side of the blade (when viewing the laryngoscope 105A from behind with the handle 120A pointed up) and the camera unit 130B on the left side of the flange. Mounting the flange 150 and the camera unit 130B on same side of the blade 125 can be advantageous because the view provided by the camera 140 is less obstructed by the insertion of the endotracheal tube than when the camera 140 is centered on the blade 125 or mounted to the right of center. The camera unit 130B could also be formed into the flange or secured adjacent to the right side of the flange.

This embodiment of the laryngoscope 105A includes a rechargeable power supply (not shown) that can be recharged through the contact points 155 in the handle 120A. Additionally, this embodiment includes a cable 160 for relaying image data to a remote viewing device (not shown). In other embodiments, the cable 160 could be used to transfer power to the camera unit 130B rather than using a rechargeable power supply.

Although not shown, the blade 125 can include a channel formed therein. This channel can be an open channel formed in the surface of the blade 125, or the channel can be formed in the body of the blade 125 so that it is enclosed. The channel can be used to provide oxygen to the patient during the intubation process. Alternatively, the channel could be used to provide suction at or near the tip of the blade 125 during the intubation process.

Figure 3:
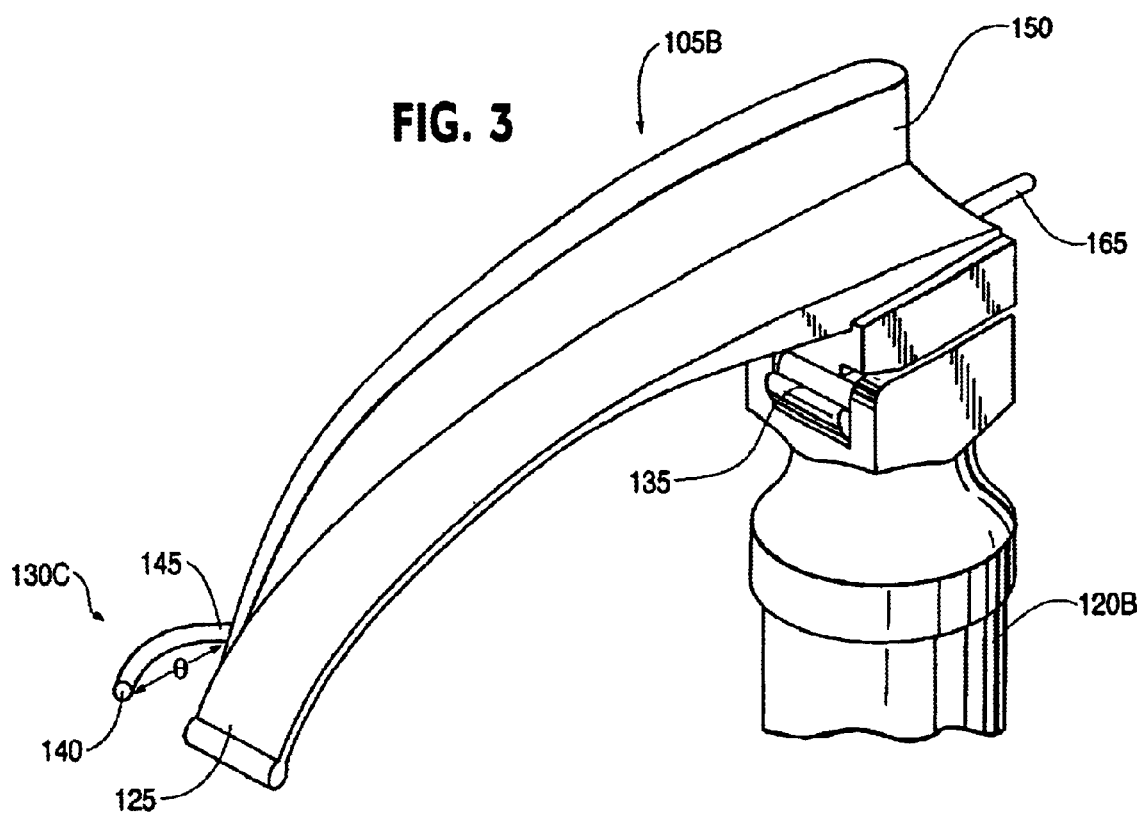
FIG. 3 illustrates an embodiment of a laryngoscope blade in accordance with the present invention.

Referring now to FIG. 3, it illustrates an embodiment of a laryngoscope 105B in accordance with the principles of the present invention. This laryngoscope 105B is wireless-enabled. Thus, images collected by the camera unit 130C can be wirelessly transmitted through the antenna 165 to a remote viewing device (not shown).

Unlike the laryngoscope 105A shown in FIG. 2, the camera unit 130C in FIG. 3 extends beyond the end of the blade 125 or stop short of the end. In other embodiments, the camera unit 130C can extend only to the end of the blade 125. Additionally, the camera unit 130C in FIG. 3 includes an offset in both the X and Y planes where the surface of the blade defines the X plane. Other embodiments, however, can include an offset in either the X or Y plane. The offset, in one embodiment, can vary in either plane from 0.05 to 1.25 inches, including all points in between. Additionally, the camera unit 130C can include a curvature, T, for better positioning the camera 140 at the end of the camera unit 130C. The curvature, T, can be a regular curvature defined by, for example, the arc of a circle, or T can represent an irregular curve.

The camera unit 130C can be formed of a rigid material to prevent any flexing and subsequent shifting of the camera 140 and its viewing angle. In other embodiments, however, the camera unit 13C can be formed of a semi-rigid material that permits the camera unit 130C to be reshaped so that the curvature angle, T, can be changed and/or the camera 140 relocated in the X and/or Y planes. Additionally, in one embodiment, the camera unit 130C can be retracted or extended to better position the camera 140 and its viewing angle.

Figure 4:
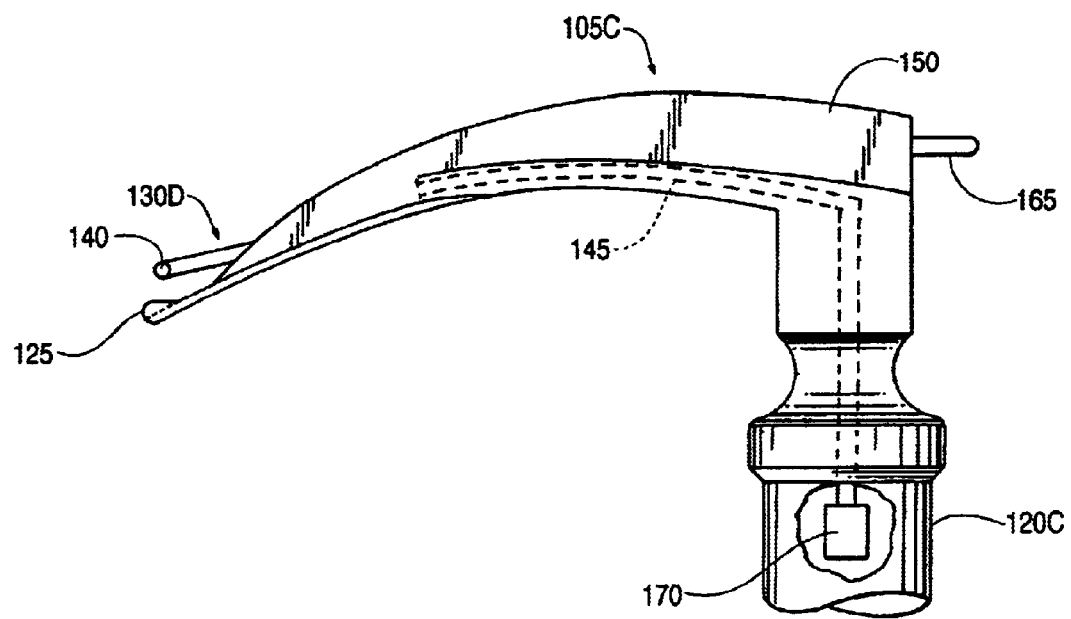
FIG. 4 illustrates a side view of an embodiment of a laryngoscope blade and a portion of a handle, both of which are constructed in accordance with the principles of the present invention.

Referring now to FIG. 4, it illustrates a side view of an embodiment of a laryngoscope 105C. In particular, this embodiment illustrates a camera controller 170 that is contained in the handle 120C of the laryngoscope 105C and connected to the camera unit 130D. The camera controller can be used to relay images to a blade-mounted, handle-mounted, or remote viewing device. This particular embodiment includes a fixed-blade rather than a removable blade.

Figure 5:
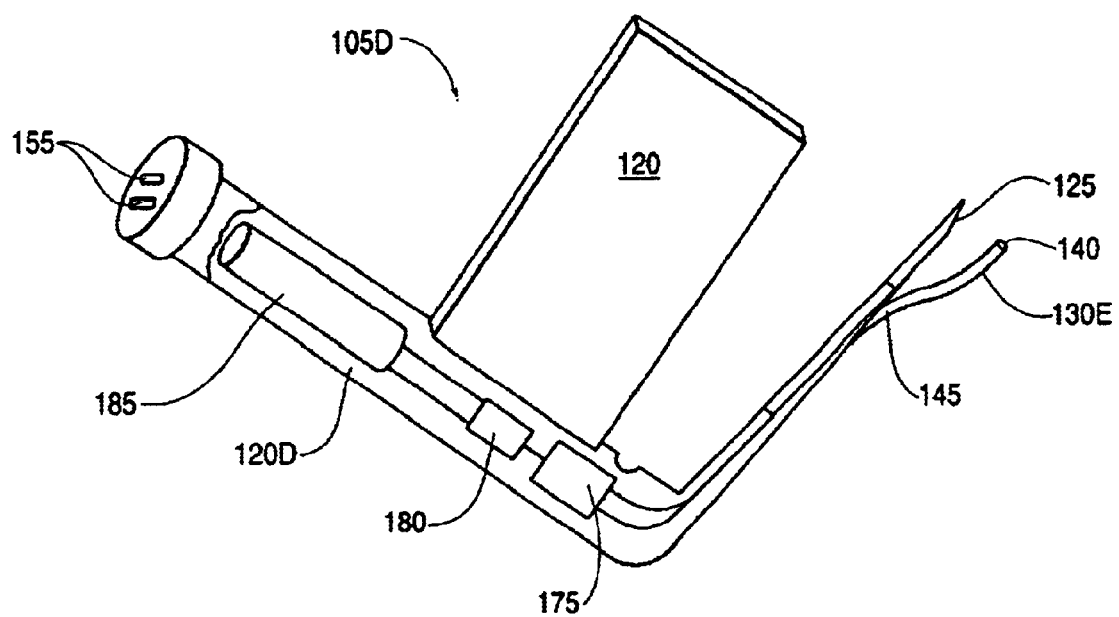
FIG. 5 illustrates a laryngoscope with an integrated viewing device in accordance with the principles of the present invention.

Referring now to FIG. 5, it illustrates another embodiment of a laryngoscope in accordance with the principles of the present invention. In this embodiment, a display is connected to the handle 120 of the laryngoscope 105D. Images captured by the camera 140 are transmitted to the camera driver 175 and relayed to the display driver 180. The display driver 180 then causes the image to be displayed. The display 170 and the camera 140 are powered by the rechargeable power supply 185. In another embodiment, the display is secured to the blade rather than to the handle. Moreover, the camera can be replaced with any type of imaging device.

In summary, embodiments of the present invention provide an optically-enabled laryngoscope with an advantageously placed imaging device for viewing a patient's airway passage. Those skilled in the art can readily recognize that numerous variations and substitutions may be made in the invention, its use, and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. An intubating scope comprising:
   a handle;
   a blade attached to the handle, the blade having a first side and a second side, wherein the first side of the blade and the second side of the blade are spaced on opposing sides of a center line running the length of the blade;

a flange attached to the first side of the blade, wherein the flange includes an inner side and an outer side, the inner side being closest to the second side of the blade and the outer side being furthest from the second side of the blade; and an imaging device attached to the blade, wherein the imaging device comprises a first portion and a second portion, the first portion being positioned adjacent to the outer side of the flange and the second portion being offset laterally from the outer side of the flange.

2. The intubating scope of claim 1, wherein the imaging device comprises:

a camera; and a transmission cable connected to the camera;

wherein the first portion of the imaging device comprises a first portion of the transmission cable and the second portion of the imaging device comprises both a second portion of the transmission cable and the camera; and wherein a curvature is defined between outer side of flange and imaging device.

3. The intubating scope of claim 1, wherein the offset between the imaging device and the blade comprises an offset in at least one of the X plane and the Y plane, wherein the X plane generally corresponds to a plane defined by a bottom side of the blade.

4. The intubating scope of claim 1, further comprising:

a display device secured to the handle, the display device being in communication with the imaging device.

5. The intubating scope of claim 1, further comprising:

a rechargeable power supply configured to power the imaging device.

6. The intubating scope of claim 1, wherein the blade comprises a front tip and wherein the camera unit extends beyond the front tip of the blade.

7. The intubating scope of claim 1, wherein the second portion of the imaging device comprises a detachment point and an end point; and wherein a curvature, $\theta$, is defined between the detachment point and the blade.

8. The intubating scope of claim 1, wherein the blade comprises:

a channel for carrying oxygen.

9. The intubating scope of claim 1, wherein the blade comprises:

a channel for providing suction to the endpoint of the blade.

10. The intubating scope of claim 1, wherein the imaging device comprises:

a fixed-focus imaging device.

11. The intubating scope of claim 1, wherein the imaging device comprises:

a variable-focus imaging device.

12. The intubating scope of claim 1, further comprising:

a wireless transmitter configured to transmit images captured by the imaging device for display on a remote viewing device.

13. The intubating scope of claim 1, wherein the imaging device comprises:

a fiber optic bundle.

14. The intubating scope of claim 1, wherein the imaging device comprises:

a camera including an angulated lens.

15. An intubating scope comprising:

a handle;

a blade attached to the handle, the blade having a left side, right side and a centerline there between;

a flange attached to the left side of the blade, the flange having a left side and a right side; and an imaging device located generally adjacent to the left side of the flange;

wherein the imaging device is angled so that it points toward the centerline of the blade.

16. The intubating scope of claim 15, further comprising:

a wireless transmitter configured to transmit images captured by the imaging device for display on a remote viewing device.

17. The intubating scope of claim 15, further comprising:

a lateral gap between the blade and the imaging device.

18. The intubating scope of claim 15, wherein the imaging device is at least partially formed into the blade.

19. The intubating scope of claim 15, wherein the imaging device is at least partially formed into the flange.

20. The intubating scope of claim 15, wherein the imaging device comprises:

an angulated lens.

21. The intubating scope of claim 20, wherein the imaging device comprises:

a fiber optic bundle connected to the angulated lens.

22. The intubating scope of claim 20, wherein the imaging device comprises:

a camera connected to the angulated lens.

23. An intubating scope comprising:

a handle;

a blade attached to the handle, the blade having a first side and a second side, wherein the first side of the blade and the second side of the blade are spaced on opposing sides of a center line running the length of the blade;

a flange attached to the second side of the blade;

a transmission cable adjacent to the second side of the blade; and an imaging device connected to the transmission cable, wherein the imaging device is pointed at an angle from the second side of the blade toward the centerline of the blade.

24. An apparatus comprising:

a blade configured to be attached to a laryngoscope handle, the blade having a first side and a second side, wherein the first side of the blade and the second side of the blade are spaced on opposing sides of a center line running the length of the blade;

a flange attached to the first side of the blade; and an imaging device connected to the flange, wherein a portion of the imaging device is pointed toward the centerline of the blade.

25. The apparatus of claim 24, wherein the imaging device is separated from the flange by a gap.

26. The apparatus of claim 24, further comprising:

an electrical contact for relaying information collected by the imaging device to a corresponding circuitry contained in the laryngoscope handle.

27. A system comprising:

a handle;

a blade attached to the handle, the blade having a first side and a second side, wherein the first side of the blade and the second side of the blade are spaced on opposing sides of a center line running the length of the blade;

a flange attached to the first side of the blade;

an imaging device adjacent to the first side of the blade, wherein the imaging device is pointed away from the flange in the lateral direction; and a display device in communication with the imaging device.

28. The system of claim 27, wherein the display comprises:

a remote display.

29. The system of claim 27, wherein the imaging device is separated from the blade by a lateral gap.

30. The system of claim 27, wherein the display is securable to the handle.

31. An intubating scope comprising:

a handle;

a blade attached to the handle, the blade having a left side and a right side;

a flange attached to the left side of the blade; and an imaging device located generally adjacent to the flange, the imaging device being separated laterally from the blade by a gap.

* * * * *